Figure 1:
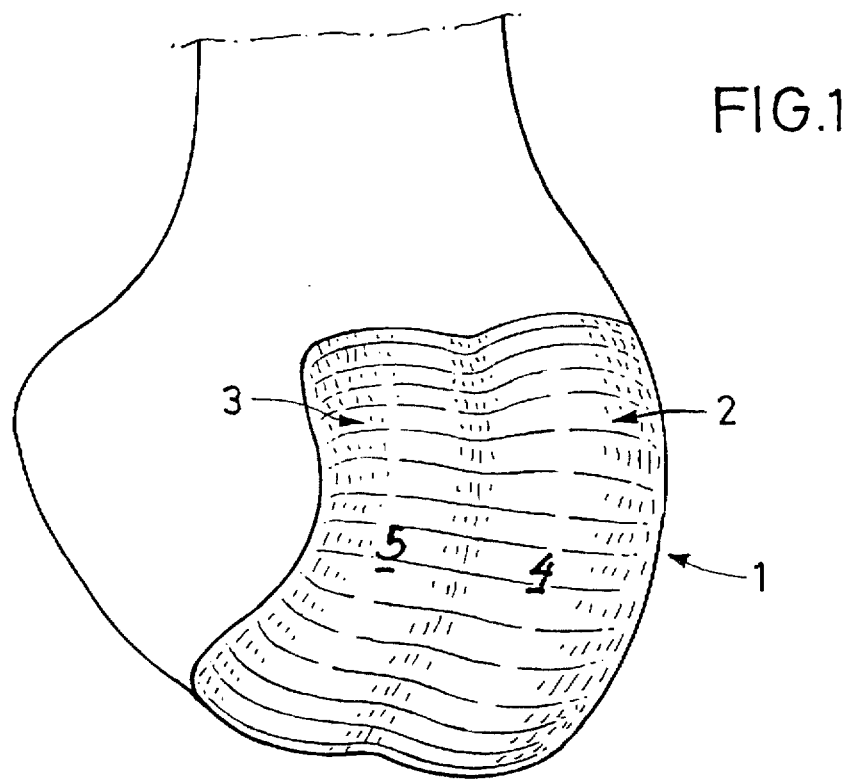

United States Patent [19]

Kubein-Meesenburg et al.

[11] Patent Number: 5,738,686
[45] Date of Patent: Apr. 14, 1998

[54] ARTIFICIAL JOINT TO REPLACE THE HUMAN PATELLA

[75] Inventors: Dietmar Kubein-Meesenburg, Kreiensen; Hans Nagerl, Klein-Lengden, both of Germany

[73] Assignee: Joachim Theusner, Munich, Germany

[21] Appl. No.: 525,717

[22] PCT Filed: Feb. 16, 1994

[86] PCT No.: PCT/EP94/00434

§ 371 Date: Nov. 17, 1994

§ 102(e) Date: Nov. 17, 1994

[87] PCT Pub. No.: WO94/22396

PCT Pub. Date: Oct. 13, 1994

[30] Foreign Application Priority Data

Apr. 3, 1993 [DE] Germany .................. 43 10 968.3

[51] Int. Cl.$^6$ .................................................. A61F 2/38
[52] U.S. Cl. ........................................................ 623/20
[58] Field of Search .............................. 623/16, 18, 20

[56] References Cited

U.S. PATENT DOCUMENTS

| | | | |
|---|---|---|---|
| 3,816,855 | 6/1974 | Saleh | 623/20 |
| 3,878,566 | 4/1975 | Bechtol | 623/20 |
| 4,151,615 | 5/1979 | Hall | 623/20 |
| 4,178,641 | 12/1979 | Grundei et al. | 623/20 |

FOREIGN PATENT DOCUMENTS

| | | |
|---|---|---|
| 021 421 | 1/1981 | Austria. |
| 0 498 586 | 12/1992 | European Pat. Off.. |
| 42 02 717 C1 | 6/1993 | Germany. |

Primary Examiner—David Isabella
Attorney, Agent, or Firm—Jones & Askew, LLP

[57] ABSTRACT

Artificial joint, especially endoprosthesis for the human patella joint, consisting of two joint bodies which move with respect to one another, one joint body (1) with two coincidental joint heads (2,3) and one joint body (6) with two coincidental joint sockets (7,8) which in each case have toroid joint surfaces (4,5; 9,10) which have functional surfaces (4,5; 9,10) which have a longitudinal plane and a corresponding transverse plane, in planes which are vertical with respect to one another, of differing, circular section contours. The curvature relationships of the functional surfaces (4,5; 9,10) are either concave-convex or convex-convex in each of the planes. The joint geometry of the functional surfaces (4,10; 5,9) which come into contact with one another, is determined by a link chain with two articulated axles, dimer link chains, with respect to one another in each of the two functional planes, which run through the middle point of the curve of the functional surfaces (4,5; 9,10) and are established by them.

11 Claims, 3 Drawing Sheets

ARTIFICIAL JOINT TO REPLACE THE HUMAN PATELLA

The present invention relates to an artificial joint, especially an endoprosthesis for the joint which connects the patella to the thigh, consisting of two joint parts with curved joint surfaces which move with respect to one another.

From German Patent Application No. P 3,908,958.4, an artificial joint is known for the replacement of human joints which consists of at least two joint parts with spherical functional surfaces which move with respect to one another. The curvature ratios of the functional surfaces which have a circular section contour, are convex-convex, convex-concave, or concave-concave with respect to one another and the joint geometry is determined by a link chain with two articulated axles, dimer link chains, which run through the centers of rotation of the functional surfaces and is defined by the centers and their distance. Here, the joint surfaces are designed in a spherical shape so that joint movement with five degrees of freedom is possible.

Nevertheless, it has been shown that such a joint is not suitable to approximate the special joint function as it is present in the human patella joint.

The object of the present invention is to create an artificial joint which is suitable to replace the human patella joint whereby the natural relationships are to be essentially reproduced.

According to the invention, this is achieved by an artificial joint consisting of two joint bodies which move with respect to one another, one joint body with two attached joint heads and one joint body with two attached joint sockets which have toroid joint surfaces in each case which have functional surfaces, in planes which are vertical with respect to one another—a longitudinal plane and a corresponding transverse plane, with different circular section contours, whereby the curvature relationships of the functional surfaces of each of the planes are either concave-convex or convex-convex, and the joint geometry of the functional surfaces which come into contact with one another is determined in each of the two functional planes by a link chain with two articulated axles, dimer link chains, which run through the middle point of the curvature of the functional surfaces and are established by them.

Thus, the invention is based on the knowledge that the joint tracks of the human patella joint can be replaced by toroid-shaped surfaces in each case of the section contours in the planes which are vertical with respect to one another.

The pressure stresses which occur in this case can be controlled by use of materials with appropriate strength. Thus, an artificial joint is created which has a particular freedom of movement in one joint plane and which simultaneously has high mechanical stability with a great range of variation for adaptation to individual situations as well as an additional ease of mobility in the transverse plane vertical to the longitudinal plane towards the lateral, due to special structural features.

Advantageous embodiments of the invention are to be found in the subclaims.

Figure 2:
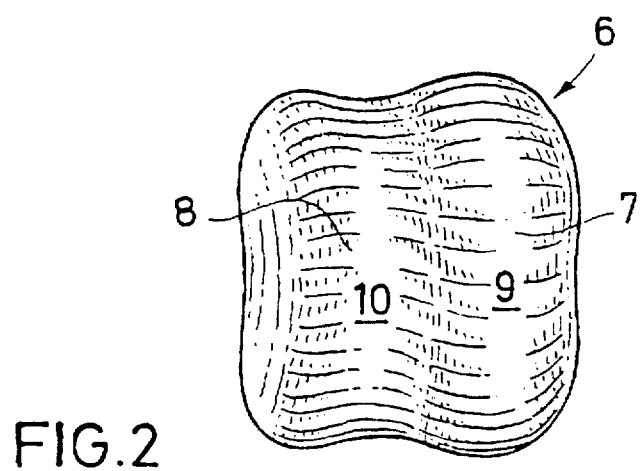
Figure 3:
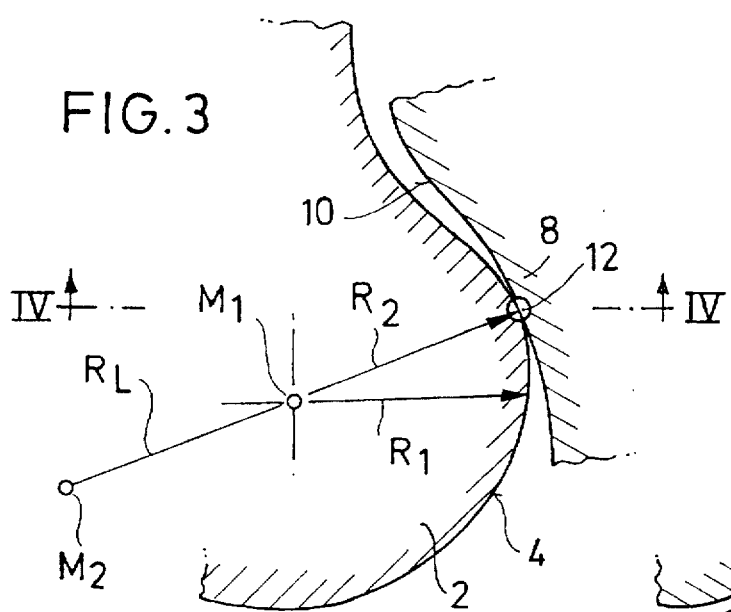
Figure 4:
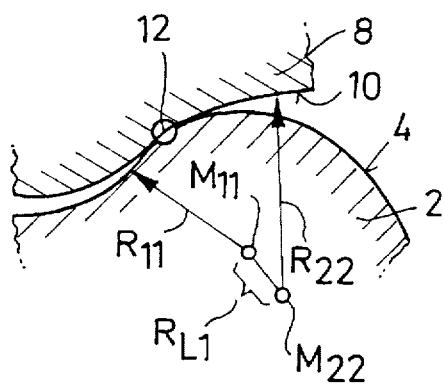
Figure 5:
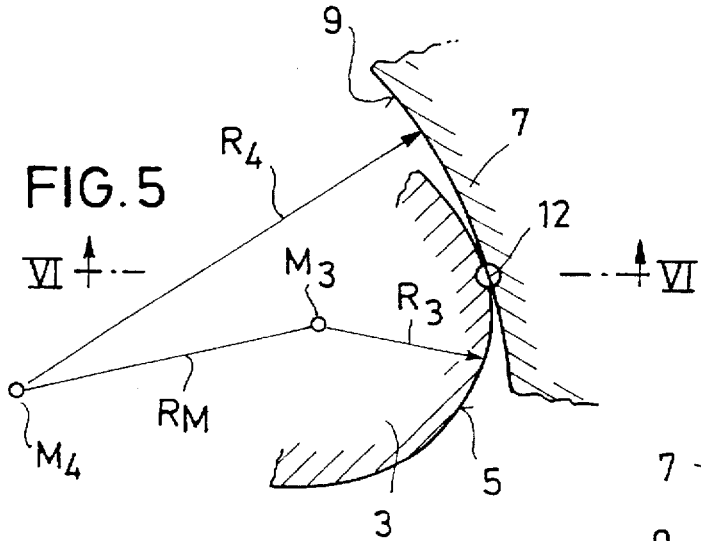
Figure 6:
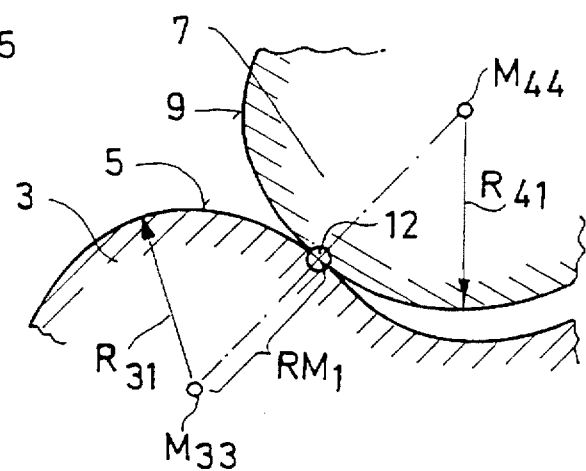
Figure 7:
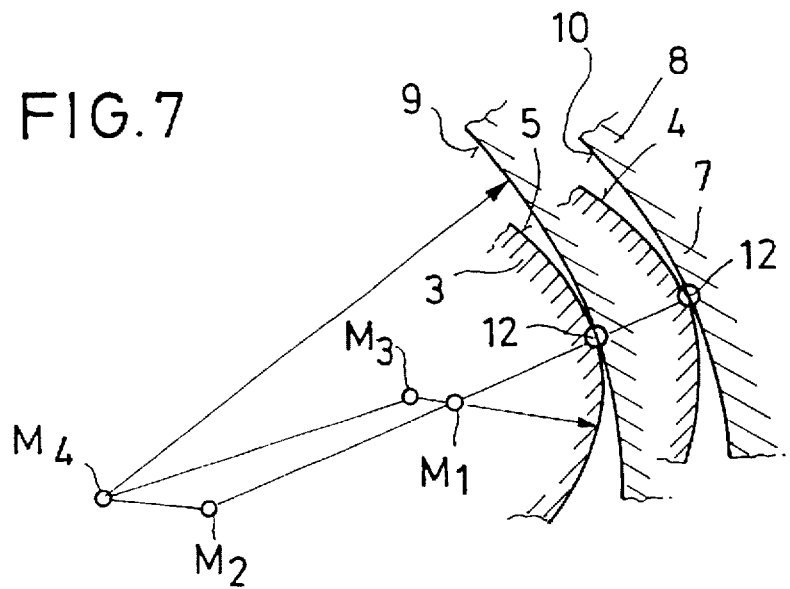

The invention is explained in more detail on the basis of the embodiment examples presented in the attached drawings. Shown are:

FIG. 1, a perspective view of a joint body according to the invention with two attached joint heads, FIG. 2, a perspective view of a joint body according to the invention with two attached joint sockets, FIG. 3, a longitudinal cut through a joint according to the invention in the area of the lateral joint part, FIG. 4, a cross section according to cut line IV—IV in FIG. 3 in the transverse plane, FIG. 5, a longitudinal cut through a joint according to the invention in the medial joint part, FIG. 6, a cut along cut line VI—VI in FIG. 5 in the transverse plane, FIG. 7, a longitudinal cut through a joint according to the invention composed of the joints according to FIGS. 3 and 5.

Figure 8:
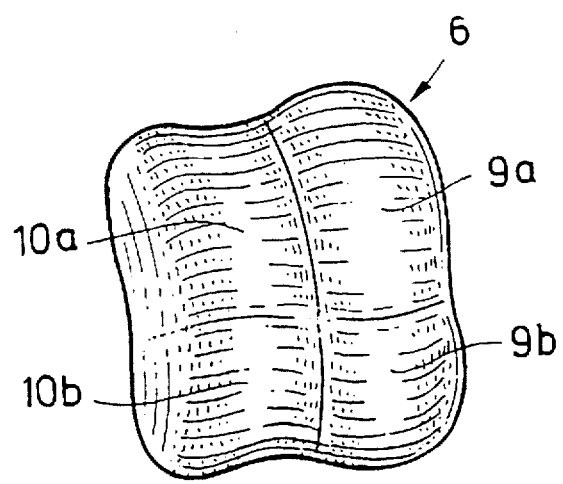

FIG. 8, a perspective view of another embodiment form of a joint body according to the invention with two attached joint sockets.

In FIG. 1, a perspective representation of a part of the hip, femur, is shown with hip joint part 1 fastened to its joint body, which consists of two adjacent joint heads, namely lateral joint head 2 and medial joint head 3. Both joint heads 2,3 have toroid functional surfaces 4,5, namely lateral functional surface 4 and medial functional surface 5 as these result in detail from the following description.

FIG. 2 shows a perspective view of patella joint part 6 which is part of hip joint part 1, which consists of two coincidental joint sockets, namely, medial joint socket 7 and lateral joint socket 8. Both joint sockets 7,8 in turn have toroid, curved functional surfaces 9,10, specifically medial functional surface 9 and lateral functional surface 10. The more detailed design is revealed in the following description. Lateral joint head 2 and lateral joint socket 8 form a lateral joint according to the invention and medial joint socket 7 and medial joint head 3 form a medial joint according to the invention.

As shown in FIG. 3, lateral functional surface 4 of lateral joint head 2, in the sagittal cut plane, that is, in the longitudinal plane, has a circular, convex section contour whose center of rotation is $M_1$ and which has radius $R_1$. Lateral joint socket 8 has functional surface 10 with a circular, concave section contour with the rotation center $M_2$ and radius $R_2$. Here, an arrangement is provided such that these centers of rotation $M_1$ and $M_2$ are inside the joint part with the convex section contour and the articulated axle tracks of the rotation centers have a radius of $RL=R_2-R_1$. Here, $R_2$ is calculated such that it is greater than $R_1$, so that an overlapping dimer link chain which is stable under pressure is represented.

In FIG. 4, it can be seen that in the transverse plane as well, the lateral functional surfaces 4,10 have circular section contours whereby the circular convex section contour of functional surface 4 has radius $R_{11}$ and the middle point or rotation center $M_{11}$ and circular, concave functional surface 10 has radius $R_{22}$ and middle point $M_{22}$. Here, both centers of rotation $M_{11}$ and $M_{22}$ lie in the body with convex functional surface 4 and the articulated axle track of the rotation centers has a radius of $RL_1=R_{22}-R_{11}$, whereby $R_{22}$ is greater than $R_{11}$ so that this arrangement represents an overlapping dimer link chain which is stable under pressure. Furthermore, it can be recognized in FIGS. 3 and 4 that the middle points, $M_{11}$ and $M_{22}$, do not coincide with rotation centers $M_1$ or $M_2$, which is advantageous. $M_2$ advantageously lies in the position of the extended leg displaced with respect to $M_1$ towards the back (caudal), whereas $M_{22}$ is displaced towards the outside in relation to $M_{11}$.

In FIG. 5, in turn, a cut is represented through the longitudinal plane or in the sagittal plane of the media joint according to the invention. Medial joint head 3 has functional surface 5 which is designed in a toroid shape and has a circular, convex section contour whereby this circular section contour has the middle point or the rotation center $M_3$ and radius $R_3$. Medial joint socket 7 has functional surface 9 which has, in the longitudinal plane, a circular, concave section contour which has middle point $M_4$ and radius $R_4$. As shown, the centers of rotation $M_3$ and $M_4$ in each case lie in the body with the concave section contour of the functional surface and the articulated axle track of the centers of rotation $M_3$ and $M_4$ has a radius of $RM=R_4-R_3$, whereby $R_4$ is greater than $R_3$ so that a dimer link chain which is stable under pressure results.

In FIG. 6, the cut according to the frontal plane, transverse plane, is indicated with respect to the presentation in FIG. 5. Here it can be recognized that in this cut plane as well, the functional surfaces 5,9 each have circular section contours. Functional surface 5 of media/joint head 3 has a circular section contour with middle point $M_{33}$ with radius $R_{31}$. Functional surface 9 of the medial joint socket has, in the transverse plane, a circular, convex section contour with the center of rotation $M_{44}$ and radius $M_{41}$. Here, the centers of rotation $M_{33}$ and $M_{44}$ in each case lie inside the appropriate joint body 3,7 and the articulated axle track of the rotation centers $M_{33}$ and $M_{44}$ has a radius of $RM_1=R_{31}+R_{41}$.

The centers of rotation, $M_3$ and $M_{33}$, must not coincide. Center $M_4$ can be displaced, relative to $M_3$, towards the distal, towards the back, and downwards, caudal, just as rotation center $M_{44}$ can be displaced, relative to $M_{33}$, forwards and outwards, lateral. The media/joint part of the patella joint according to the invention is designed in such a way that it should replace the natural articulation between the inner joint part of the thigh (femur) and the inner portion of the knee cap (patella). Here, this joint has, in the sagittal plane (the longitudinal plane), an overlapping, compressioned-actuated dimer chain and in the transverse plane or planes which are vertical with respect to it, a nonoverlapping, compression-actuated link chain. Due to the toroid-shaping of the joint surfaces, good freedom of movement with force actuation in the longitudinal plane is provided and to a large extent eliminated in the transverse plane.

Resulting from FIGS. 1 and 2, in each case, the medial and lateral joint parts are connected to one another such that in each case, a rigid connection is provided between the joint heads and the joint sockets. Here, it is advantageous that in the transverse plane or planes, convex joint heads 2,3 are connected through a matched concave structure and in the transverse plane or planes, joint sockets 7,8 are connected through a matched, convex structure. Here it is expedient when the radius of the connecting, convex structure between the joint heads 2,3 is not identical with the radii $R_{44}$ and $R_{22}$. The radius of the convex structure which connects joint sockets 7,8 can be greater than that of the concave, connecting structure of joint heads 2,3. Through the coupling of the joint heads and the joint sockets, the medial and lateral joint parts are to be arranged with respect to one another so that the rotational axes run parallel to one another, vertical to the longitudinal plane, and are arranged with respect to one another so that the medial rotational axes are arranged behind the lateral rotational axes in each case, and in the longitudinal plane, as a functional orientation, a four-bar joint is created according to the invention. The rotational axes of the toroid surfaces can also be positioned inclined towards one another.

In the embodiment form according to FIGS. 1 to 6, the radii. $R_1$, $R_2$, $R_3$ and $R_4$, are selected so that they make a predominantly harmonious transition into the guiding structures of the patella. It is further expected, by the calculation of the radii, that they assure that the contact points which move around $M_1$ describe a significantly greater path than the contact points which move around $M_3$. Here, the contact points in each case represent the points at which the functional surfaces lying opposite one another touch. Furthermore, the middle points $M_1$ and $M_2$ with respect to one another, and middle points $M_2$ and $M_4$ with respect to one another, as well as $M_2$ and $M_4$ with respect to $M_1$ and $M_2$ are selected such that in the start position of the state of the human knee, the contact points in the lateral as well as medial joint part lie to a large extent in an almost horizontal transverse plane. With increasing bend, the contact points lie in the different transverse planes, and the contact moves on the lateral joint part of the patella more quickly towards the cranial than towards the medial part of the patella. In the other direction, the contact points with increasing bend on the medial joint head part run more quickly towards caudal, in order to lose contact in a deep bend.

FIG. 7 shows a longitudinal cut through a joint according to the invention composed of a medial joint and a lateral joint, whereby the medial joint is arranged behind the lateral joint. The joint position at the beginning of a knee bend is shown. Furthermore, the same parts as in FIGS. 3 and 5 are provided with the same reference numbers. Here, it can be recognized that the lateral joint, seen in the longitudinal plane, is displaced towards the front. Likewise, it is possible to displace the lateral joint towards the front and downwards with respect to the medial joint.

In FIG. 8, another embodiment form of joint sockets 9,10 of patella joint part 6 is represented. Here, it can be recognized that the functional surface of the medial joint socket and the lateral joint socket in each case are divided into two overlapping partial functional surfaces, 9a,9b, and 10a,10b. The fundamental geometric form of the functional surfaces 9a,9b, and 10a,10b corresponds to that of functional surfaces 9 and 10 according to FIGS. 2 and 4. Here, a hump-shaped transition results between the partial functional surfaces. The middle points of the circular section contours of lateral functional surfaces 10a,10b lie in the same plane. The same applies to the middle points of medial functional surfaces 9a and 9b. To the extent that it is a matter of the circular section contour in the transverse plane of the functional surfaces, no change occurs with respect to the embodiment form in FIGS. 2 and 6. In the representations of FIGS. 2 and 8, middle degree 12 between functional surfaces 9 and 10 or 9a,9b, and 10a,10b, in each case is represented with medium bending, that is, the ends in each case are displaced laterally. Likewise, the straight design of this middle degree falls within the scope of the invention.

Furthermore, it is within the scope of the invention when, deviating from the embodiment example of FIG. 6, functional surface 9 has, in the transverse plane, a concave, circular section contour, so that a dimer link chain which is stable under pressure forms, whereby the radius of the articulated axle track is $RM_1=R_{41}-R_{31}$, with $R_{41}>R_{31}$, whereby the middle points $M_{33}$ and $M_{44}$ lie in the joint body with the convex section contour. A corresponding design can also be provided for functional surfaces 9a,9b in FIG. 8.

We claim:

1. An endoprosthesis for the human patella joint, comprising:

first and second joint bodies operatively associated with each other to move with respect to one another;

the first joint body having two attached joint heads (2,3) with toroid-shaped functional surface sections (4,5), and the second joint body having two attached joint sockets (7,8) also with toroid-shaped functional surface sections (9,10), each functional surface section having a longitudinal plane and a transverse plane which are vertical with respect to one another and which have differing circular section contours;

the attached joint heads (2,3) of the first joint body being operatively associated with the attached joint sockets (7,8) of the second joint body so that one said joint head (2) and one said joint socket (8) constitute a lateral joint of the prosthesis and the other said joint head (3) and the other said joint socket (7) constitute a medial joint of the prosthesis;

one of the lateral joint head (2) and the lateral joint socket (8) has a circular convex section contour whose center of rotation is $M_1$ and whose radius is $R_1$;

the other of the lateral joint head (2) and the lateral joint socket (8) has a circular concave section contour with a center of rotation $M_2$ and radius $R_2$;

viewed in the longitudinal plane, the medial joint has the medial joint head (3) with a toroid-shaped functional surface section (5) having a circular, convex section contour with a rotation center $M_3$ and radius $R_3$, and the medial joint socket (7) with a functional surface section (9) having a circular, concave section contour with a rotation center $M_4$ and radius $R_4$;

the functional surface sections (4,5; 9,10) have respective longitudinal and transverse rotation centers ($M_1,M_{11}$; $M_2,M_{22}$; $M_3,M_{33}$; and $M_4,M_{44}$);

the longitudinal centers of rotation ($M_1$, $M_2$, $M_3$, and $M_4$) lie within the joint part with the convex section contours;

the joint geometry of the functional sections (4,10; 5,9) which contact one another is through a link chain with two articulated axles which extend through and are defined by the rotation centers ($M_1,M_{11}$; $M_2,M_{22}$; $M_3,M_{33}$; and $M_4,M_{44}$) of the respective joint curvatures; and the radii $R_1$, $R_2$, $R_3$, and $R_4$ are selected so that the surface contact points that move around the center of rotation $M_1$ describe a substantially greater path than the contact points that move around the center of rotation $M_3$, where the surface contact points in each case are the points at which the functional surfaces lying opposite one another are mutually touching.

2. Artificial joint according to claim 1, wherein:

the centers of rotation lie within the joint part with the convex section contour; and articulated axle tracks of the center of rotation have a radius $RL=R_2-R_1$, whereby $R_2-R_1$, whereby $R_2$ is greater than $R_1$.

3. Artificial joint according to claim 1 in the transverse plane, the lateral functional surface section (4) of the lateral joint head (2) and the lateral functional surface section (10) of the joint socket (8) have a circular section contour whereby the circular, convex section contour of the functional surface section (4) has radius $R_{11}$ and middle point $M_{11}$, and the circular, concave functional surface section (10) has radius $R_{22}$, and center of rotation $M_{22}$;

and the centers of rotation $M_{11}$ and $M_{22}$ lie in the body with the convex functional surface section (4) and the articulated axle track of the rotation centers has a radius of $RL_1=R_{22}-R_{11}$, whereby $R_{22}$ is greater than $R_{11}$.

4. Artificial joint according to claim 3, wherein the center of rotation $M_{11}$ and $M_{22}$, do not coincide with the centers of rotation $M_1$ or $M_2$, and $M_2$ is displaced backwards, regarded in the position of the extended leg, with respect to $M_1$, so that $M_{22}$ is displaced outwards in relation to $M_{11}$.

5. Artificial joint according to claim 2, the centers of rotation $M_3$ and $M_4$, lie with the convex section contour of the functional surface section; and the articulated axle track of the rotation centers $M_3$ and $M_4$ have a radius of $RM=R_4-R_3$, wherein $R_4$ is greater than $R_3$.

6. Artificial joint according to claim 5, wherein:

in the section through the transverse plan the functional surface section (5) of the joint head (3) and the functional surface section (9) of the joint socket (7) each have circular section contours whereby the functional surface section (5) of the joint head (3) has a convex section contour with middle point $M_{33}$ and radius $R_{31}$, and the functional surface section (9) of the medial joint socket has a circular convex section contour with middle point $M_{44}$ and radius $R_{41}$ middle points $M_{33}$ and $M_{44}$ each are located inside the corresponding joint body (3,7); and the articulated axle track of the rotation centers $M_{33}$ and $M_{44}$ has a radius of $RM_1=R_{31}+R_{41}$.

7. Artificial joint according to claim 6, wherein the rotation center $M_4$ is displaced, relative to rotation center $M_3$, towards the back and downwards, caudal; and rotation center $M_{44}$ is displaced, relative to rotation center $M_{33}$, towards the front and towards the outside, lateral.

8. Artificial joint according to claim 1, wherein:

in the transverse planes, the convex joint heads (2,3) are connected through a matched concave structure;

and in the transverse p, the joint sockets (7,8) are connected through a matched, convex structure whereby the radius of a connecting convex structure between the convex joint heads (2,3) is not identical with the radii $R_{44}$ and $R_{22}$, and the radius of the convex structure connecting the joint sockets (7,8) is greater than that of the concave, connecting structure of the joint heads (2,3).

9. Artificial joint according to claim 1, wherein the centers of rotation $M_1$ and $M_2$, with respect to one another and the centers of rotation $M_2$ and $M_4$ with respect to one another, as well as centers of rotation $M_2$ and $M_4$ with respect to the centers of rotation $M_1$ and $M_2$, are selected so that in starting position of the human knee, the contact points in the lateral and in the medial joint part substantially lie in an almost horizontal transverse plane.

10. Artificial joint according to claim 1, wherein the joint socket (9,10) of the patella joint part (6) has functional surface sections which are divided into two overlapping partial functional surfaces (9a,9b) and (10a,10b) an the circular section contour of these partial functional surfaces corresponds to that of the corresponding functional surface section of the joint socket (9,10).

11. Artificial joint according to claim 1, wherein the functional surface section (9) seen in the transverse plane, has a concave, arched section contour whereby the radius of the articulated axle track is $RM_1=R_{41}-R_{31}$, with $R_{41}>R_{31}$, whereby the middle points $M_{33}$ and $M_{44}$, lie in the joint body with the convex section contour.

* * * * *

UNITED STATES PATENT AND TRADEMARK OFFICE
CERTIFICATE OF CORRECTION

PATENT NO. : 5,738,686

DATED : April 14, 1998

INVENTOR(S) : Kubein-Meesenburg, et al.

It is certified that error appears in the above-identified patent and that said Letters Patent is hereby corrected as shown below:

In column 5, line 48, delete "whereby $R_2 - R_1$,".

Column 6, line 12, "plan" should be --plane--.

Column 6, line 33, "p" should be --plane--.

Signed and Sealed this

Eleventh Day of August 1998

Attest:

BRUCE LEHMAN

Attesting Officer

Commissioner of Patents and Trademarks